United States Patent
Okamura

(10) Patent No.: US 10,920,075 B2
(45) Date of Patent: Feb. 16, 2021

(54) HYDROLYSIS-RESISTANT SILICONE COMPOUND AND A METHOD FOR PRODUCING THE SAME

(71) Applicant: SHIN-ETSU CHEMICAL CO., LTD., Tokyo (JP)

(72) Inventor: Kaoru Okamura, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/096,621

(22) PCT Filed: Apr. 17, 2017

(86) PCT No.: PCT/JP2017/015470
§ 371 (c)(1),
(2) Date: Oct. 25, 2018

(87) PCT Pub. No.: WO2017/188046
PCT Pub. Date: Nov. 2, 2017

(65) Prior Publication Data
US 2019/0136059 A1 May 9, 2019

(30) Foreign Application Priority Data
Apr. 27, 2016 (JP) .................... 2016-089068

(51) Int. Cl.
| | |
|---|---|
| *C08L 83/04* | (2006.01) |
| *C07F 7/18* | (2006.01) |
| *G02C 7/04* | (2006.01) |
| *A61L 27/18* | (2006.01) |
| *A61L 27/50* | (2006.01) |
| *C08F 30/08* | (2006.01) |

(52) U.S. Cl.
CPC ............. *C08L 83/04* (2013.01); *A61L 27/18* (2013.01); *A61L 27/50* (2013.01); *C07F 7/18* (2013.01); *C08F 30/08* (2013.01); *G02C 7/04* (2013.01)

(58) Field of Classification Search
CPC .................... C08G 77/20; C08F 290/068
See application file for complete search history.

(56) References Cited

U.S. PATENT DOCUMENTS

| | | | | |
|---|---|---|---|---|
| 3,808,178 | A | * 4/1974 | Gaylord | ........... C08F 220/12 |
| | | | | 526/279 |
| 4,120,570 | A | 10/1978 | Gaylord | |
| 4,665,145 | A | 5/1987 | Yokota et al. | |
| 4,759,991 | A | 7/1988 | Kanno et al. | |
| 5,714,557 | A | 2/1998 | Kunzler et al. | |
| 2006/0229423 | A1* | 10/2006 | Parakka | ........... C07F 7/0874 |
| | | | | 528/37 |
| 2008/0081850 | A1 | 4/2008 | Fujisawa et al. | |
| 2009/0299022 | A1 | 12/2009 | Ichinohe | |
| 2012/0114729 | A1 | 5/2012 | Stabler et al. | |
| 2014/0128564 | A1 | 5/2014 | Fujisawa et al. | |

FOREIGN PATENT DOCUMENTS

| | | |
|---|---|---|
| CN | 101541315 A | 9/2009 |
| CN | 102690419 A | 9/2012 |
| JP | 50-87184 | 7/1975 |
| JP | 60-20910 A | 2/1985 |
| JP | 60-163908 A | 8/1985 |
| JP | 2000-502329 A | 2/2000 |
| JP | 2008-202060 A | 9/2008 |
| JP | 2008-537966 A | 10/2008 |
| JP | 2010-505030 A | 2/2010 |
| JP | 2011-503242 A | 1/2011 |

(Continued)

OTHER PUBLICATIONS

Shimizu (Chemistry Letters 22(10) (1993) 1807-1810).*
Extended European Search Report, dated Oct. 25, 2019, for European Application No. 17789331.0.
Thomson Scientific, Database WPI, WE 201280, AN 2012-N13732, London, GB, Oct. 2, 2012, 4 pages, XP002795027.
International Search Report issued in PCT/JP2017/015470 (PCT/ISA/210), dated Jul. 18, 2017.
Written Opinion of the International Searching Authority issued in PCT/JP2017/015470 (PCT/ISA/237), dated Jul. 18, 2017.
Shimizu, N., et al, "Prediction of Structural Effects of Trialkylsilyl Groups on Reactivity toward Nucleophilic Displacement at Silicon," Chemistry Letters, 1993, vol. 22, No. 10, pp. 1807-1810.

*Primary Examiner* — Kuo Liang Peng
(74) *Attorney, Agent, or Firm* — Birch, Stewart, Kolasch & Birch, LLP

(57) ABSTRACT

A polymerizable monomer compound is disclosed, which can produce a polymer having advantageous transparency and high oxygen permeability for use as an ophthalmic device, while exhibiting sufficient resistance to hydrolysis. A silicone compound of the following formula (1) is described:

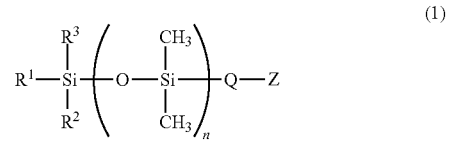

(1)

where the residue $R^1R^2R^3Si$— has a steric parameter value of −1.00 or less, the parameter indicating the steric bulkiness of the unsubstituted hydrocarbon groups bonded to the silicon atom, and in a case where at least one of $R^1$, $R^2$ and $R^3$ is a substituted hydrocarbon group, the steric parameter value of the residue in which each of the functional group and halogen atom bonded to the carbon atom of the substituted hydrocarbon group is supposed to be substituted with a hydrogen atom is −1.00 or less. Methods for producing the monomer compound, and methods for preparing the silicone compound are also described.

13 Claims, No Drawings

(56) References Cited

FOREIGN PATENT DOCUMENTS

| KR | 10-2012-0107435 A | 10/2012 |
|----|-------------------|---------|
| WO | WO 97/20851 A1 | 6/1997 |
| WO | WO 2006/102050 A2 | 9/2006 |
| WO | WO 2008/042158 A1 | 4/2008 |
| WO | WO 2008/042163 A1 | 4/2008 |
| WO | WO 2009/032266 A2 | 3/2009 |
| WO | WO 2010/121024 A2 | 10/2010 |

\* cited by examiner

HYDROLYSIS-RESISTANT SILICONE COMPOUND AND A METHOD FOR PRODUCING THE SAME

TECHNICAL FIELD

The present invention relates to a chemical compound suitable for manufacturing ophthalmic devices, such as contact lenses, intraocular lenses and artificial corneas, and a method for producing such a compound. More specifically, the present invention relates to a compound and a method for producing such a compound, which can be polymerized with one or more other polymerizable monomers, such as (meth) acrylic monomers, to give a polymer suitable for use in ophthalmic applications with improved resistance to hydrolysis.

BACKGROUND ART

A variety of silicone compounds are known as a monomer for manufacturing ophthalmic devices. For example, 3-[tris(trimethylsiloxy)silyl]propylmethacrylate (TRIS) of the formula shown below is widely used as a monomer for manufacturing soft contact lenses. Polymers obtained by copolymerization of TRIS with a hydrophilic monomer, such as N,N-dimethylacrylamide or N-vinyl-2-pyrrolidone, are advantageous in that they are transparent and have high oxygen permeability. However, since the siloxane bond is susceptible to hydrolysis, the siloxane moieties tend to decompose gradually in contact with a compound having an active hydrogen, such as water or alcohols, leading to degraded physical properties of contact lenses during prolonged storage.

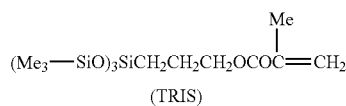

(TRIS)

JP-A 2011-503242 discloses a silicone monomer with improved resistance to hydrolysis, which is a compound having a terminal tri(alkylsiloxy)silyl or di(alkylsiloxy)silyl group, such as 3-[tris(n-butyldimethylsiloxy)silyl]propylmethacrylate shown below:

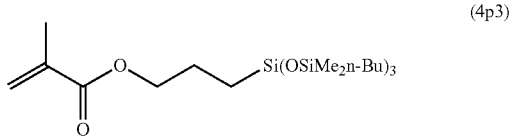

(4p3)

In recent years, there is a demand for high oxygen permeability in ophthalmic polymers so as to make continuous wearing possible for a prolonged period of time. In order to provide an ophthalmic device with high oxygen permeability, a monomer compound is required to have a large mass fraction of the Si moieties. However, the compound described in JP-A 2011-503242 has a low content of siloxane, resulting in polymers having insufficient oxygen permeability.

Several monomer compounds are known to give polymers with high oxygen permeability. For example, JP-A 2008-202060 discloses such a monomer compound for manufacturing ophthalmic devices, which has the following formula:

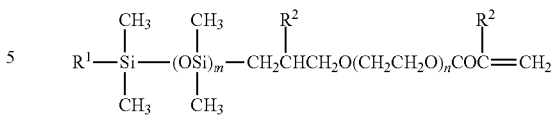

(d)

wherein m is an integer of from 3 to 10, n is either 1 or 2, $R^1$ is an alkyl group having 1 to 4 carbon atoms, and $R^2$ is either a hydrogen atom or a methyl group.

LIST OF PRIOR ART

Patent Literature

[Patent Literature 1] JP-A 2011-503242
[Patent Literature 2] JP-A 2008-202060

SUMMARY OF THE INVENTION

However, a polymer comprising the compound described in JP-A 2008-202060 as a monomer component shows insufficient resistance to hydrolysis, so that the physical properties of ophthalmic devices made of such a polymer may change due to hydrolysis. Thus, one object of the invention is to provide a polymerizable monomer compound having a predetermined number of silicon atoms, and capable of giving a polymer having advantageous transparency and high oxygen permeability for use as an ophthalmic device, while exhibiting sufficient resistance to hydrolysis. Another object of the invention is to provide a method for producing such a monomer compound.

Through extensive investigation to achieve the above objects, the present inventor has found that the hydrolysis resistance can be improved by end-capping a siloxane terminal of a dimethyl(poly) siloxane structure with a triorganosilyl group having specific steric bulkiness, and has completed the invention.

Thus, in one aspect, the present invention provides a silicone compound of the following formula (1):

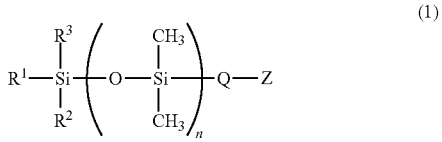

(1)

wherein Z is a radically polymerizable moiety; Q is a substituted or unsubstituted, divalent hydrocarbon group having 1 to 20 carbon atoms, and optionally comprising one or more bonds selected from the group consisting of an amide bond, an ether bond, an ester bond and an unsaturated bond; n is an integer of from 1 to 100; and $R^1$, $R^2$ and $R^3$ are each an unsubstituted, saturated or unsaturated, monovalent hydrocarbon group having 1 to 20 carbon atoms, or a substituted form of the monovalent hydrocarbon group in which a part or all of the hydrogen atoms bonded to the carbon atoms are each substituted with a functional group and/or a halogen atom; and
wherein the residue $R^1R^2R^3Si—$ has a steric parameter value of $-1.00$ or less, the parameter indicating the steric bulkiness of the unsubstituted hydrocarbon groups bonded to the silicon atom and, in a case where at least one of $R^1$, $R^2$ and $R^3$ is a substituted hydrocarbon group, the steric parameter value of the residue in which each of the functional group and halogen atom bonded to the carbon atom of the substituted hydrocarbon group is supposed to be substituted with a hydrogen atom is −1.00 or less.

The present invention also provides a method for preparing the silicone compound.

The silicone compound according to the invention provides a colorless and transparent polymer having high oxygen permeability with improved resistance to hydrolysis. Therefore, the silicone compound and the method for producing the same according to the invention are suitable for manufacturing ophthalmic devices.

DESCRIPTION OF PREFERABLE EMBODIMENTS

The silicone compound according to the invention is represented by the following formula (1):

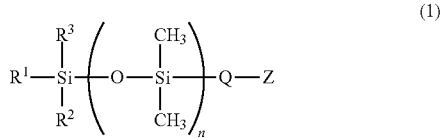

(1)

wherein Z is a radically polymerizable moiety; Q is a substituted or unsubstituted, divalent hydrocarbon group having 1 to 20 carbon atoms, and optionally comprising one or more bonds selected from the group consisting of an amide bond, an ether bond, an ester bond and an unsaturated bond; n is an integer of from 1 to 100; and $R^1$, $R^2$ and $R^3$ are each an unsubstituted, saturated or unsaturated, monovalent hydrocarbon group having 1 to 20 carbon atoms, or a substituted form of the monovalent hydrocarbon group in which a part or all of the hydrogen atoms bonded to the carbon atoms are each substituted with a functional group and/or a halogen atom.

The silicone compound of the formula (1) is characterized in that all of the substituents bonded to the silicon atoms at sites other than at the terminals are a methyl group, and that the terminal organosilyl group (i.e., $R^1R^2R^3Si$—) has a bulky steric structure. By configuring the structure of the siloxane moiety in this manner, the hydrolysis resistance of the silicone compound can be improved, whereby a stable polymer can be obtained.

In the formula (1) shown above, $R^1$, $R^2$ and $R^3$ are each an unsubstituted, saturated or unsaturated, monovalent hydrocarbon group having 1 to 20 carbon atom, preferably 1 to 10 carbon atoms, and more preferably 1 to 8 carbon atoms, or a substituted form of the monovalent hydrocarbon group in which a part or all of the hydrogen atoms bonded to the carbon atoms are each substituted with a functional group and/or a halogen atom. Examples of the unsubstituted monovalent hydrocarbon group include an alkyl group, such as methyl, ethyl, propyl, butyl, pentyl, hexyl, heptyl, octyl, nonyl and decyl groups; a cycloalkyl group, such as cyclopentyl and cyclohexyl groups; an aryl group, such as phenyl and tolyl groups; an alkenyl group, such as vinyl and allyl groups; and an aralkyl group, such as benzyl group. A part or all of the hydrogen atoms bonded to the carbon atoms of these groups may be substituted with a functional group, such as hydroxy group, hydroxyalkyl group, amino group, aminoalkyl group, amide group, alkylamide group, alkoxy group, alkoxyalkyl group, alkoxycarbonyl group, and alkoxycarbonylalkyl group; and/or a halogen atom, such as chlorine and fluorine atoms. Preferably, $R^1$, $R^2$ and $R^3$ are an alkyl group of 1 to 6 carbon atoms, a phenyl group, or a substituted form of the aforementioned group in which a part or all of the hydrogen atoms bonded to the carbon atoms are each substituted with a fluorine atom. $R^1$, $R^2$ and $R^3$ each may be selected from the foregoing so that their combination gives an $R^1R^2R^3Si$— residue that satisfies the steric parameter described in more detail below. In particular, $R^1$, $R^2$ and $R^3$ are each preferably selected from an alkyl group of 2-8 carbon atoms, more preferably of 2-4 carbon atoms. When the number of carbon atoms is larger, the steric hindrance becomes larger, but the proportion of the siloxane moiety decreases, so that the characteristics derivable from the siloxane may decline.

Taft's steric parameter is known as an indication of steric bulkiness of a hydrocarbon group (substituent or R). This parameter indicates the steric bulkiness (three-dimensional extent) of a hydrocarbon group (substituent). For example, Taft's parameters of hydrocarbon groups bonded to a silicon atom are described in Shimizu, N. et al., "A Quantitative Scale for the Structural Effect on Reactivity toward Nucleophilic Displacement at Silicon"; Chemistry Letters (1992), 21(7), p. 1263-1266; and Shimizu, N. et al., "Prediction of Structural Effects of Trialkylsilyl Groups on Reactivity toward Nucleophilic Displacement at Silicon"; Chemistry Letters (1993), 22(10), p. 1807-1810.

The steric parameter is represented by the following equation (a):

$$S(A) = \log k_{rel} \tag{a}$$

wherein $\log k_{rel}$ is a logarithmic value of a hydolysis rate of an organochlorosilane ($R^1R^2R^3SiCl$), relative to trimethylchlorosilane in an 89 mol % aqueous 1,4-dioxane solution at 25° C.; and "A" denote substituent R.

It is also known that this steric parameter satisfies the equations (b), (c), (d) and (e) shown below, and it is possible to estimate a value of a steric parameter for a silicon atom having various substituents.

$$S(ACH_2) = 0.205(A) - 0.57 \tag{b}$$

$$S(A^1A^2A^3C) = S(A^1CH_2) + 1.6S(A^2CH_2) + 4.0S(A^3CH_2) \tag{c}$$

$$S(AO) = 0.39S(A) - 0.34 \tag{d}$$

$$S(A^1A^2A^3Si) = S(A^1) + 1.15S(A^2) + 1.35S(A^3) \tag{e}$$

It is noted that $S(A^1CH_2)$ is greater than $S(A^2CH_2)$, and $S(A^2CH_2)$ is greater than $S(A^3CH_2)$. It is also noted that $S(A^1)$ is greater than $S(A^2)$, and $S(A^2)$ is greater than $S(A^3)$. The smaller the steric parameter is, the greater the steric hindrance on the silicon atom is.

Steric parameter values of trialkylsiliy groups are given in Shimizu, N. et al., "Prediction of Structural Effects of Trialkylsilyl Groups on Reactivity toward Nucleophilic Displacement at Silicon"; Chemistry Letters (1993), 22(10), p. 1807-1810. For example, steric parameter values of $RMe_2Si$ groups, wherein R is methyl, ethyl, n-propyl, n-butyl, isopropyl or t-butyl, are shown in Table 1 below. It is seen from the values listed below that the larger the absolute value is, the greater the steric hindrance is.

TABLE 1

| Substituent R in an RMe₂Si group | Steric parameter |
| --- | --- |
| Me | 0.00 |
| Et | −0.57 |
| n-Pr | −0.68 |
| n-Bu | −0.71 |
| i-Pr | −1.48 |
| t-Bu | −3.76 |

The steric parameter values of $R^1R^2R^3Si$ groups are shown in Table 2 below, where the $R^1R^2R^3Si$ group is di(n-butyl)methylsilyl group, tri(n-butyl)silyl group, triethylsilyl group, diphenylmethylsilyl group, tri(isopropyl)silyl group or tri(t-butyl)silyl group.

TABLE 2

| $R^1R^2R^3Si$ group | Steric parameter |
| --- | --- |
| (n-Bu)₂MeSi | −1.53 |
| (n-Bu)₃Si | −2.49 |
| Et₃Si | −2.00 |
| Ph₂MeSi | −1.83 |
| (i-Pr)₃Si | −5.18 |
| (t-Bu)₃Si | −13.16 |

According to the present invention, the three dimensional structure of the organosilyl group (i.e., $R^1R^2R^3Si$—) is specified by the aforementioned steric parameter. The silicone compound according to the invention is characterized in that the residue $R^1R^2R^3Si$— has a steric parameter value of −1.00 or less, preferably −1.50 or less, more preferably −2.00 or less.

As shown in Tables 1 and 2 above, none of trimethylsilyl, ethyldimethylsilyl, n-propyldimethylsilyl and n-butyldimethylsilyl groups satisfies the parameter value specified in the present invention. These organosilyl groups have small steric bulk, so that silicone compounds having such a terminal structure do not exhibit satisfactory resistance to hydrolysis.

A preferable structure that satisfies the steric parameter requirement may be one in which at least one of $R^1$, $R^2$, and $R^3$ is a group selected from isopropyl, t-butyl, phenyl, 1,1,2,2-tetramethylpropyl and trifluoropropyl groups. Another preferable structure may be one in which all of $R^1$, $R^2$ and $R^3$ are the same group selected from ethyl, n-propyl, isopropyl and n-butyl groups.

Particularly preferable structures are shown below.

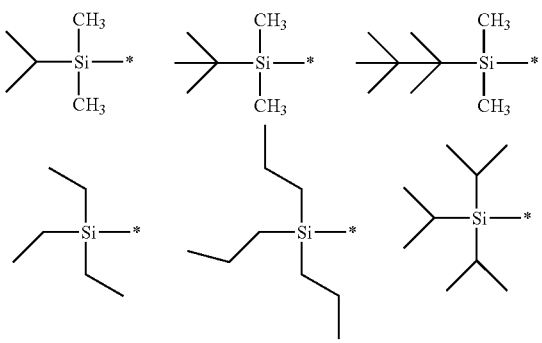

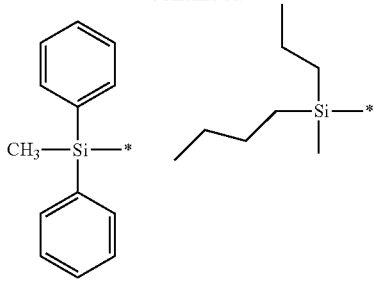

In these formulas, the site indicated by "*" is bound to the oxygen atom.

As described above, the steric parameter value is to specify the steric bulkiness of the terminal triorganosilyl group in the silicone compound according to the invention. In a case where at least one of $R^1$, $R^2$ and $R^3$ is a substituted hydrocarbon group, the steric parameter value of the residue in which each of the functional group and halogen atom bonded to the carbon atom of the substituted hydrocarbon group is supposed to be substituted with a hydrogen atom is −1.00 or less, preferably −1.50 or less, more preferably −2.00 or less. As described above, examples of the functional group include hydroxy group, hydroxyalkyl group, amino group, aminoalkyl group, amide group, alkylamide group, alkoxy group, alkoxyalkyl group, alkoxycarbonyl group, and alkoxycarbonylalkyl group. Examples of the halogen atom include chlorine, fluorine, and bromine. Particularly preferable compounds are those in which one or more of the hydrogen atoms bonded to the carbon atoms of the aforementioned groups are each substituted with a halogen atom, such as a fluorine atom. An example thereof is shown below.

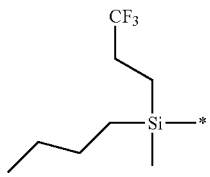 [SMILES: *[Si](C)(CCCC)CCC(F)(F)F]

In the above formula, the site indicated by "*" is bound to the oxygen atom. In this case, the steric parameter of the group in which each fluorine atom is supposed to be substituted with a hydrogen atom should satisfy the above requirement. In other words, the steric parameter value of a terminal n-butyl-methyl-3,3,3-trifluoropropylsilyl group is the same as that of a n-butyl-methyl-propylsilyl group having a propyl group in place of the 3,3,3-trifluoropropyl group.

In the formula (1) shown above, Q is a substituted or unsubstituted, divalent hydrocarbon group having 1 to 20 carbon atoms, which may optionally comprise one or more bonds selected from the group consisting of an amide bond, an ether bond, an ester bond and an unsaturated bond. Examples of the divalent hydrocarbon group include ethylene, 1,3-propylene, 1-methylpropylene, 1,1-dimethylpropylene, 2-methylpropylene, 1,2-dimethylpropylene, 1,1,2-trimethylpropylene, 1,4-butylene, 2-methyl-1,4-butylene, 2,2-dimethyl-1,4-butylene, 3-methyl-1,4-butylene, 2,2-diethyl-1,4-butylene, 2,3-dimethyl-1,4-butylene, 2,2,3-trimethyl-1,4-butylene, 1,5-pentylene, 1,6-hexanylene, 1,7-heptanylene, 1,8-octanylene, 1,9-nonanylene, 1,10-decanylene groups; a substituted form of the aforementioned group in which a part or all of the hydrogen atoms bonded to the carbon atoms are each substituted with a hydroxy group, a hydroxyalkyl group, an amino group, an aminoalkyl group, an amide group, an alkylamide group, an alkoxy group, an alkoxyalkyl group, an alkoxycarbonyl group, or an alkoxycarbonylalkyl group; and a halogenated aklylene groups substituted with a halogen atom such as chlorine or fluorine. Examples of the group containing an ether bond include a polyalkylene oxide, such as polyethylene oxide, polypropylene oxide, and polyethylene-propylene oxide.

Preferably, Q is represented by the following formula (2) or (3):

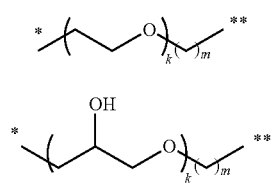

(2)

(3)

wherein k is an integer of from 0 to 6, m is an integer of from 1 to 4 when k equals zero, or "m" is an integer of from 1 to 17, preferably an integer of from 1 to 4, when k is not zero, with the proviso that $1 \leq k+m \leq 20$, the site indicated by "*" is bonded to the silicon atom in the formula (1); and the site indicated by "**" is bound to the moiety Z in the formula (1). Preferably, k=1 and m=an integer of 1 to 4, or k=0 and m=an integer of 1 to 4.

Preferably, Q is an unsubstituted, divalent hydrocarbon that does not contain oxygen nor nitrogen atom, i.e., k=0 in the formula (2) or (3) above. In this case, Q is preferably a methylene, ethylene, propylene or butylene group, and more preferably a propylene group.

In the formula (1) shown above, Z is a radically polymerizable moiety. Examples of the radically polymerizable moiety include groups having an acryl or methacryl group, such as acryloyloxy, methacryloyloxy, acrylamide and methacrylamide groups; N-vinylamide, alkynyl, styryl, indenyl, alkenyl, cycloalkenyl, norbornyl, and conjugated or non-conjugated alkanediene groups. Among others, acryloyloxy, methacryloyloxy, acrylamide, methacrylamide, N-vinylamide and styryl groups are preferred. In view of the ease of reaction, groups having an acryl and methacryl group are preferred, with acryloyloxy or methacryloyloxy groups being especially preferred.

In the formula (1) shown above, n is an integer of from 1 to 100, more preferably an integer of from 2 to 20, still more preferably an integer of from 3 to 10, and most preferably 4. If the value of n is less than the lower limit, the oxygen permeability of the resulting polymer will be low. If the value of n exceeds the upper limit shown above, the hydrophilicity of the resulting polymer will be low.

The silicone compound according to the invention can provide a polymer having improved resistance to hydrolysis, by virtue of its three-dimensional structure in which the residue $R^1R^2R^3Si-$ satisfies the steric parameter requirement as discussed above. The hydrolysis resistance may be evaluated, for example, by a gas chromatography (GC) analysis. More specifically, the hydrolysis resistance may be evaluated by an area in percentage of the compound measured in GC after heated in a water/2-propanol solution containing 5% by weight of acetic acid at 80° C. for 168 hours, relative to an area (100%) of the compound measured in GC at the initiation of the heat treatment (0 hour). The silicone compound of the invention may show an area of 80% or more after the heat treatment, relative to an area (100%) at the initiation of the heat treatment (0 hour).

In another aspect, the present invention provides a method for preparing a silicone compound of the formula (1) shown above. The compound of the formula (1) may be prepared by reacting a siloxane of the following formula (4):

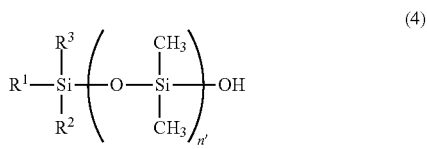

(4)

wherein $R^1$, $R^2$ and $R^3$ are as defined above, and n' is n−1; with a halogenated silyl compound of the formula (5):

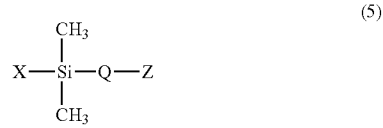

(5)

wherein Q and Z are as defined above, and X is a halogen atom.

The compound of formula (4) shown above may be prepared by reacting a silanol compound of the following formula:

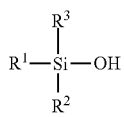

wherein $R^1$, $R^2$, and $R^3$ are as defined above;
with an organometallic compound, and then with hexamethylcyclotrisiloxane to cause ring-opening polymerization.

Alternatively, the compound of formula (4) shown above may be prepared by reacting a cyclic siloxane of the following formula:

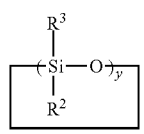

wherein y is an integer of from 3 to 20, and $R^2$ and $R^3$ are as defined above;
with an organometallic compound, and then with hexamethylcyclotrisiloxane to cause ring-opening polymerization.

Preferably, $R^1$, $R^2$ and $R^3$ have no hydroxyl group. This is because the presence of a hydroxyl group may cause an undesirable side reaction on its active hydrogen site during the reaction between the above-mentioned compound and the organometallic compound.

The organometallic compound is a polymerization initiator, and can be any of those conventionally used for ring-opening polymerization of a cyclic siloxane. For example, it may be an organomagnesium compound or an organolithium compound. An organomagnesium compound is a compound having a carbon-magnesium bond and a magnesium-halogen bond. An organolithium compound is a compound having a carbon-lithium bond. Such a compound may be any compound known in the art. Examples of the organolithium compound include methyllithium, ethyllithium, butyllithium, phenyllithium, benzyllithium and the like. In particular, an organolithium compound diluted in a hydrocarbon compound such as hexane or cyclohexane is preferable, and a solution of n-butyllithium in hexane is more preferable in view of ease of handling and availability.

The above-mentioned reactions may be carried out in a method known in the art. For example, an organometallic compound in an amount of at most one molar equivalent may be added to the silanol compound or the cyclic siloxane compound mentioned above to cause a reaction, followed by dropwise addition of hexamethylcyclotrisiloxane for a further reaction. For example, the reaction of butyldimethylsilanol with BuLi results in the formation of BuMe$_2$SiOLi. Then, the product thus formed may be used as an initiator for ring-opening reaction of hexamethylcyclotrisiloxane to obtain a compound of the formula (4) shown above. Further, a halogenated silyl compound is added for a further reaction to obtain a silicone compound of the formula (1) shown above. The addition of the organometallic compound, hexamethylcyclotrisiloxane, and the halogenated silyl compound may be typically carried out at a temperature in the range of from about 0° C. to about 25° C. There is no particular limitation on the reaction temperature, but it is preferable that the temperature does not exceed a boiling point of the solvent used. The completion of the reaction with hexamethylcyclotrisiloxane may be confirmed, after the dropwise addition and aging at an elevated temperature, by checking the presence or absence of hexamethylcyclotrisiloxane, e.g., by the disappearance of its peak in GC. By confirming the completion of the reaction by the GC measurement, a silicone compound of higher purity, free of residual hexamethylcyclotrisiloxane, can be obtained.

The amount of the organometallic compound to be added may range from 0.1 molar equivalent to 1 molar equivalent, relative to the silanol compound. If the amount of the organometallic compound is larger than the upper limit indicated above, side reactions of the organometallic compound occur, which is undesirable. If the amount the organometallic compound is less than the lower limit indicated above, the reaction rate with hexamethylcyclotrisiloxane is too slow, which is undesirable.

There is no particular limitation on the solvent that may be used for the aforesaid reactions. For example, a hydrocarbon solvent, such as hexane and heptane; an aromatic solvent, such as toluene; an ether solvent, such as tetrahydrofuran; a ketone solvent, such as methyl ethyl ketone and N,N-dimethylformamide; and an ester solvent, such as ethyl acetate, may be suitably used.

The amount of the halogenated silyl compound to be added is preferably such that the molar ratio of the halogenated silyl compound to the compound of formula (4) ranges from 0.8 to 2.0, more preferably from 0.9 to 1.5, and still more preferably from 1.0 to 1.2

Purification may be carried out after the completion of the reaction in a conventional manner. For example, the product may be isolated by washing the organic layer with water, and then removing the solvent. It is also possible to use vacuum distillation or activated carbon treatment.

In an exemplary production method according to the invention, a silanol compound or a cyclic siloxane compound is diluted with 50% by mass of toluene, and then 1 molar equivalent of n-butyllithium (n-hexane solution) is added. Subsequently, hexamethylcyclotrisiloxane dissolved in 200% by mass of tetrahydrofuran is added. The reaction is completed after about 3 hours at room temperature. The progress of the reaction may be confirmed by monitoring hexamethylcyclotrisiloxane, e.g., by GC. After the reaction with hexamethylcyclotrisiloxane, 1 molar equivalent of a halogenated silyl compound is added, and allowed to react at room temperature for about 1 hour and the reaction is completed. Then, the organic layer is washed with water. The organic layer is recovered when the pH of the washing solution becomes near neutral (pH=6-8). The solvent and any unreacted raw material that may be present in the organic layer are distilled off under reduced pressure to yield a silicone compound of the formula (1) indicated above.

The silicone compound according to the invention can provide a polymer having repeating units derived by addition polymerization of the radically polymerizable moiety of the silicone compound. The silicone compound has good compatibility with another compound (hereinafter referred to as a polymerizable monomer or a hydrophilic monomer) having a group that is polymerizable with the radically polymerizable functional group of the silicone compound, such as (meth)acryl group. Therefore, the silicone compound may be copolymerized with such a polymerizable monomer to provide a colorless and transparent copolymer. It is also possible to polymerize the present silicone compound only. As described above, the compound of the invention provides a polymer having improved hydrolysis resistance. Further, the silicone compound has good compatibility with a (meth)acrylic monomer having a fluorine substituent(s) for imparting stain resistance, and can therefore provide a polymer with improved stain resistance (antifouling property). In the production of a copolymer comprising repeating units derived from copolymerization of the silicone compound of the invention and another polymerizable (hydrophilic) monomer, the silicone compound of the invention may be used in an amount of 50-90 parts by mass, more preferably in an amount of 60-80 parts by mass, based on 100 parts by mass of the total of the (hydrophilic) monomer and the silicone compound of the invention.

Examples of the polymerizable monomer include acrylic monomers, such as (meth)acrylic acid, methyl (meth)acrylate, ethyl (meth)acrylate, (poly)ethylene glycol dimethacrylate, polyalkylene glycol mono(meth)acrylate, polyalkylene glycol monoalkylether (meth)acrylate, trifluoroethyl (meth)acrylate, 2-hydroxyethyl (meth)acrylate, 2,3-dihydroxypropyl (meth)acrylate; acrylic acid derivatives, such as N,N-dimethyl acrylamide, N,N-diethyl acrylamide, N-acryloyl morpholine, N-methyl (meth)acrylamide; and other unsaturated aliphatic and aromatic compounds, such as crotonic acid, cinnamic acid, vinyl benzoic acid; and silicone monomers having one or more polymerizable groups such as (meth)acryl group. The monomer may be used alone or in combination.

Copolymerization of the compound of the invention with the another polymerizable monomer(s) as described above may be carried out in any method known in the art. For example, it may be carried out using a polymerization initiator known in the art, such as a thermal polymerization initiator or a photopolymerization initiator. Examples of the polymerization initiator include 2-hydroxy-2-methyl-1-phenyl-propan-1-on, azobisisobutyronitrile, azobisdimethylvaleronitrile, benzoyl peroxide, tert-butyl hydroperoxide, and cumene hydroperoxide. The polymerization initiator may be used alone or in combination. The amount of the polymerization initiator may be from 0.001 to 2 parts by mass, preferably from 0.01 to 1 part by mass, based on 100 parts by mass of the total polymerizable components A (co)polymer comprising repeating units derived from the compound of the invention has excellent oxygen permeability, and improved resistance to hydrolysis. Accordingly, the (co)polymer is suitable for manufacturing ophthalmic devices such as contact lenses, intraocular lenses and artificial corneas. There is no particular limitation with respect to a method for preparing an ophthalmic device using the (co)polymer, and any conventional method known in the art for manufacturing ophthalmic devices may be used. For example, a machining process and a molding process may be used for forming a lens shape such as a contact lens and an intraocular lens.

EXAMPLES

The present invention will be further explained in more detail with reference to the following Examples and Comparative Examples, which should not to be construed to limit the scope of the present invention.

In the Examples below, viscosities were measured with a Cannon-Fenske viscometer, and specific gravities were measured with a hydrometer. Refractive indices were measured with a digital refractometer, RX-5000 (Atago Co. Ltd.). $^1$H-NMR analysis was conducted with JNM-ECP5000 (JEOL Ltd.), using deuterochloroform as a solvent for measurement.

The compounds' purities shown below were determined by gas chromatography carried out under the following conditions.

Conditions for Gas Chromatography i. Apparatus and Parameters

Apparatus: Agilent GC system 7890A. Detector: flame ionization detector (FID). Column: J&W HP-5MS (0.25 mm×30 m×0.25 μm). Carrier gas: helium. Constant flow rate: 1.0 ml/min. Injected sample volume: 1.0 μL. Split ratio: 50:1. Inlet temperature: 250° C. Detector temperature: 300° C.

ii. Temperature Regime

Initial temperature: 50° C. Initiation period: 2 min. Gradient: 10° C./min. Termination temperature: 250° C. (holding time: 10 minutes).

iii. Sample Preparation

A sample solution was placed directly into a GC vial without dilution.

Example 1

A 2-liter, three-neck eggplant flask equipped with a Dimroth condenser, a thermometer and a dropping funnel was charged with 112.0 g of t-butyldimethylsilanol and 56.0 g of toluene. Then, 289.0 g of a solution of n-butyllithium in hexane was added dropwise from the dropping funnel. After the completion of the dropwise addition, the reaction mixture was stirred at room temperature for 1 hour, and the disappearance of the starting material was confirmed by gas chromatography as an indication of the completion of the reaction. After the completion of the reaction, 245.3 g of hexamethylcyclotrisiloxane and 537.6 g of THF were added and stirred at room temperature for 3 hours, and the disappearance of hexamethylcyclotrisiloxane was confirmed by gas chromatography as an indication of the completion of the reaction. After the completion of the reaction, 196.0 g of methacryloyloxypropyldimethylchlorosilane, 4.26 g of triethylamine and 0.025 g of 2,6-di-t-butyl-4-methylphenol were added and stirred at room temperature for 1 hour. After the completion of the reaction, the organic layer was transferred to a separatory funnel and washed five times with tap water. The organic layer was recovered, and the solvent and unreacted raw materials were distilled off under reduced pressure at an internal temperature of 90° C. to obtain a silicone compound of the formula (6) shown below. The yield was 426.5 g. The silicone compound thus obtained had a purity of 97.2% as determined by GC analysis, a viscosity of 6.6 mm$^2$/s (25° C.), a specific gravity of 0.933 (25° C.), and a refraction index of 1.4242. The $^1$H-NMR data were as follows:

0.0 ppm (30H), 0.6 ppm (2H), 0.9 ppm (9H), 1.7 ppm (2H), 2.0 ppm (3H), 4.1 ppm (2H), 5.5 ppm (1H), 6.1 ppm (1H).

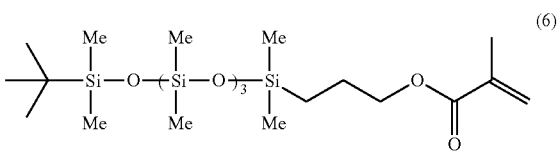

The steric parameter of the terminal t-butyldimethylsilyl group is −3.76.

Example 2

The procedures of Example 1 were repeated, except that triethylsilanol was used in place of t-butyldimethylsilanol to obtain a silicone compound of the formula (7) shown below. The yield was 389.2 g. The silicone compound thus obtained had a purity of 95.4% as determined by GC analysis, a viscosity of 5.3 mm$^2$/s (25° C.), a specific gravity of 0.937 (25° C.), and a refraction index of 1.4246. The $^1$H-NMR data were as follows:

0.0 ppm (24H), 0.6 ppm (8H), 0.8 ppm (9H), 1.7 ppm (2H), 2.0 ppm (3H), 4.1 ppm (2H), 5.5 ppm (1H), 6.1 ppm (1H).

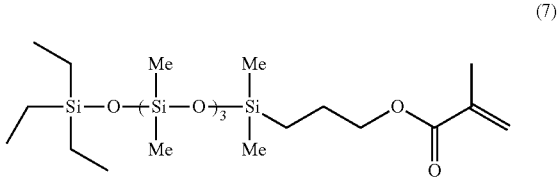

The steric parameter of the terminal triethylsilyl group is −2.00.

Example 3

The procedures of Example 1 were repeated, except that triisopropylsilanol was used in place of t-butyldimethylsilanol to obtain a silicone compound of the formula (8) shown below. The yield was 411.6 g. The silicone compound thus obtained had a purity of 95.1% as determined by GC analysis, a viscosity of 6.9 mm$^2$/s (25° C.), a specific gravity of 0.943 (25° C.), and a refraction index of 1.4341. The $^1$H-NMR data were as follows:

0.0 ppm (24H), 0.6 ppm (5H), 1.0 ppm (18H), 1.7 ppm (2H), 2.0 ppm (3H), 4.1 ppm (2H), 5.5 ppm (1H), 6.1 ppm (1H).

(8)

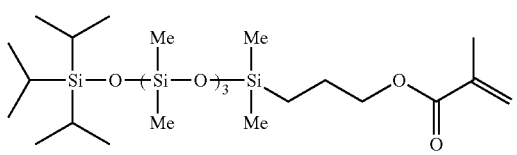

The steric parameter of the terminal triisopropylsilyl group is −5.18.

Example 4

A 2-liter, three-neck eggplant flask equipped with a Dimroth condenser, a thermometer and a dropping funnel was charged with 88.8 g of 2,4,6,8-tetramethyl-2,4,6,8-tetrapropylcyclotetrasiloxane and 44.4 g of toluene. Then, 285.6 g of a solution of n-butyllithium in hexane was added dropwise from the dropping funnel. After the completion of the dropwise addition, the reaction mixture was stirred at room temperature for 1 hour, and the disappearance of the starting material was confirmed by gas chromatography as an indication of the completion of the reaction. After the completion of the reaction, 193.5 g of hexamethylcyclotrisiloxane and 268.8 g of THF were added and stirred at room temperature for 3 hours, and the disappearance of hexamethylcyclotrisiloxane was confirmed by gas chromatography as an indication of the completion of the reaction. After the completion of the reaction, 155.1 g of methacryloyloxypropyldimethylchlorosilane, 3.36 g of triethylamine and 0.025 g of 2,6-di-t-butyl-4-methylphenol were added and stirred at room temperature for 1 hour. After the completion of the reaction, the organic layer was transferred to a separatory funnel and washed five times with tap water. The organic layer was recovered, and the solvent and unreacted raw materials were distilled off under reduced pressure at an internal temperature of 90° C. to obtain a silicone compound of the formula (9) shown below. The yield was 345.3 g. The silicone compound thus obtained had a purity of 96.3% as determined by GC analysis, a viscosity of 5.7 mm²/s (25° C.), a specific gravity of 0.923 (25° C.), and a refraction index of 1.4274. The ¹H-NMR data were as follows:
0.0 ppm (27H), 0.6 ppm (6H), 0.9 ppm (6H), 1.3 ppm (6H), 1.7 ppm (2H), 2.0 ppm (3H), 4.1 ppm (2H), 5.5 ppm (1H), 6.1 ppm (1H).

(9)

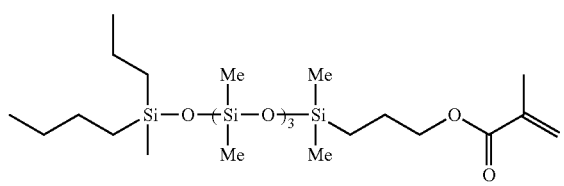

The steric parameter of the terminal n-butyl-methyl-propyl-silyl group is −1.49.

Example 5

The procedures of Example 3 were repeated, except that 2,4,6-tetramethyl-2,4,6-tris(3,3,3-trifluoropropyl)cyclotrisiloxane was used in place of 2,4,6,8-tetramethyl-2,4,6,8-tetrapropylcyclotetrasiloxane to obtain a silicone compound of the formula (10) shown below. The yield was 381.2 g. The silicone compound thus obtained had a purity of 96.4% as determined by GC analysis, a viscosity of 6.9 mm²/s (25° C.), a specific gravity of 1.003 (25° C.), and a refraction index of 1.4140. The ¹H-NMR data were as follows:
0.0 ppm (27H), 0.6 ppm (4H), 0.7 ppm (2H), 0.9 ppm (3H), 1.3 ppm (4H), 1.7 ppm (2H), 2.0 ppm (3H), 2.1 ppm (2H), 4.1 ppm (2H), 5.5 ppm (1H), 6.1 ppm (1H).

(10)

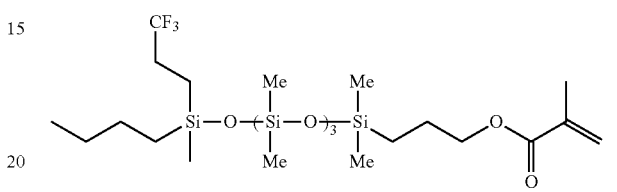

The steric parameter of the terminal n-butyl-methyl-3,3,3-trifluoropropylsilyl group is −1.49, which is the same as that of n-butyl-methyl-propylsilyl group having a propyl group in place of the 3,3,3-trifluoropropyl group.

Comparative Examples 1 and 2

In Comparative Examples 1 and 2, silicone compounds of the following formula (11) or (12) were used, both of which are widely used as monomers for soft contact lenses.

(11)

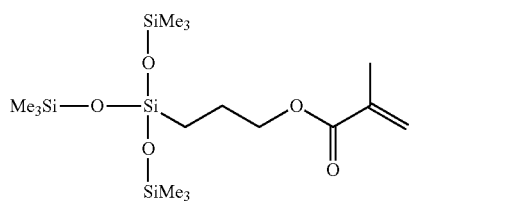

The steric parameter of the terminal trimethylsilyl group is 0.

(12)

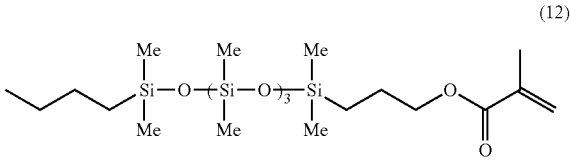

The steric parameter of the terminal n-butyldimethylsilyl group is −0.71.
Evaluation Test
Evaluation of Hydrolysis Resistance For each of the silicone compounds obtained above, the following test was conducted. In a 20-ml screw tube, 0.1 g of the silicone compound, 2-propanol (3.90 g), acetic acid (0.24 g), distilled water (0.90 g) and 2,6-di-t-butyl-methylphenol (2 mg, as a polymerization inhibitor) were placed and thoroughly mixed. Then, the screw tube was sealed, and held at 80° C. for 168 hours. The mixed solution was subjected to gas chromatography immediately after the mixing (0 hour) and after 168 hours from the mixing. The conditions for the gas chromatography were as described above.

The peak areas in gas chromatography is proportional to the amounts of components contained in the sample. The weight loss due to hydrolysis was evaluated by a peak area (%) of the silicone compound after 168 hours, relative to the peak area (100%) of the silicone compound immediately after the mixing (0 hour). The results are shown in Table 3 below.

TABLE 3

|  | Compound # | Steric Parameter | Area in GC (%) |
|---|---|---|---|
| Ex. 1 | (6) | −3.76 | 85.8 |
| Ex 2 | (7) | −2.00 | 84.1 |
| Ex. 3 | (8) | −5.18 | 89.3 |
| Ex. 4 | (9) | −1.49 | 81.9 |
| Ex. 5 | (10) | −1.49 | 83.8 |
| C. Ex. 1 | (11) | 0 | 51.9 |
| C. Ex. 2 | (12) | −0.71 | 62.0 |

As shown in Table 3, the silicone compounds of Comparative Examples 1 and 2 underwent hydrolysis while being held at 80° C. for 168 hours under the aforesaid conditions, as indicated by the significantly decreased levels thereof. In contrast, the silicone compounds according to the invention showed superior hydrolysis resistance with a small decrease in the peak area percentage. The silicone compound of the invention has a polysiloxane structure and, accordingly, can be copolymerized with another polymerizable monomer to give a transparent and colorless cured product with excellent oxygen permeability.

The silicone compound of the invention has improved hydrolysis resistance. Accordingly, the silicone compound of the invention provides a colorless and transparent polymer having high oxygen permeability with improved resistance to hydrolysis. The silicone compound and the method for producing the same according to the invention are useful for manufacturing ophthalmic devices, e.g., contact lenses, intraocular lenses and artificial corneas.

The invention claimed is:

1. A silicone of the following formula (1):

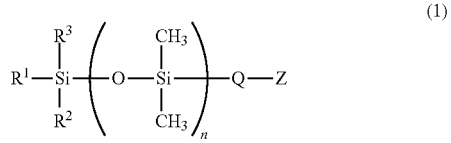

wherein Z is a radically polymerizable moiety; Q is represented by the following formula (2) or (3):

wherein "k" is an integer of from 0 to 6, "m" is an integer of from 1 to 4 when "k" equals zero, or "m" is an integer of from 1 to 17 when "k" is not zero, with the proviso that 1≤3k+m≤20, the site indicated by "*" is bonded to the silicon atom in the formula (1); and the site indicated by "**" is bonded to the moiety Z in the formula (1);

n is an integer of from 4 to 100; and $R^1$, $R^2$ and $R^3$ are each an unsubstituted, saturated or unsaturated, monovalent hydrocarbon group having 1 to 20 carbon atoms, or a substituted form of the monovalent hydrocarbon group in which a part or all of the hydrogen atoms bonded to the carbon atoms are each substituted with a functional group and/or a halogen atom, wherein the residue $R^1R^2R^3Si-$ has a steric parameter value of −1.00 or less, the parameter indicating the steric bulkiness of the unsubstituted hydrocarbon groups bonded to the silicon atom, and in a case where at least one of $R^1$, $R^2$ and $R^3$ is a substituted hydrocarbon group, the steric parameter value of the residue in which each of the functional group and halogen atom bonded to the carbon atom of the substituted hydrocarbon group is supposed to be substituted with a hydrogen atom is −1.00 or less.

2. The silicone of claim 1, wherein Z is a moiety comprising an acryloyl or methacryloyl group.

3. The silicone of claim 1, wherein the $R^1R^2R^3Si-$ residue has a steric parameter value of −1.50 or less.

4. The silicone of claim 3, wherein the residue $R^1R^2R^3Si-$ has a steric parameter value of −2.00 or less.

5. The silicone of claim 1, wherein at least one of $R^1$, $R^2$ and $R^3$ is selected from isopropyl, t-butyl, phenyl and trifluoropropyl groups.

6. The silicone of claim 1, wherein all of $R^1$, $R^2$ and $R^3$ are the same group selected from ethyl, n-propyl, isopropyl and n-butyl groups.

7. The silicone of claim 1, wherein the residue $R^1R^2R^3Si-$ is selected from the following:

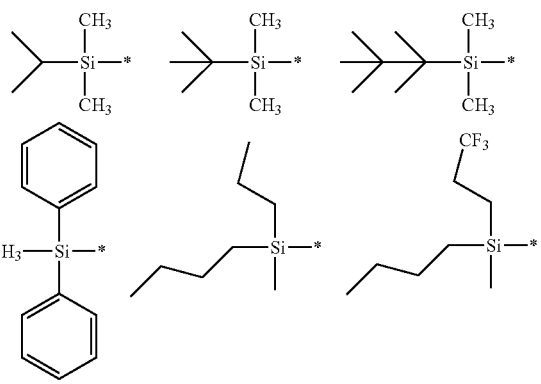

wherein the site indicated by "*" is bonded to the oxygen atom.

8. The silicone of claim 1, wherein "k" is 1, and "m" is from 1 to 4.

9. The silicone of claim 1, wherein "k" is 0, and "m" is from 1 to 4.

10. A polymer comprising a repeating unit derived from addition polymerization of the radically polymerizable moiety Z of the silicone as defined in claim 1.

11. A copolymer comprising a repeating unit derived from polymerization of the radically polymerizable moiety Z of the silicone as defined in claim 1 with one or more other compounds having a group that is polymerizable with the radically polymerizable moiety Z.

12. An ophthalmic device comprised of the copolymer of claim 11.

13. A method for preparing a silicone of claim 1, said method comprising:

reacting a siloxane of the following formula (4):

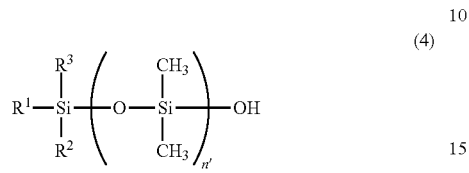

(4)

wherein $R^1$, $R^2$, and $R^3$ are as defined above, and n' is n−1; with a halogenated silyl compound of the formula (5):

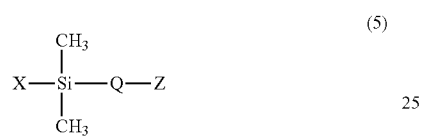

(5)

wherein Q and Z are as defined above, and X is a halogen atom;

to obtain the silicone of the formula (1).

\* \* \* \* \*